United States Patent [19]

Wiesehahn et al.

[11] Patent Number: 4,791,062

[45] Date of Patent: Dec. 13, 1988

[54] FVR VACCINE

[75] Inventors: Gary P. Wiesehahn, Alameda; Richard E. Giles, Union City; David R. Stevens, Fremont, all of Calif.

[73] Assignee: Diamond Scientific Co., Des Moines, Iowa

[21] Appl. No.: 70,201

[22] Filed: Jul. 6, 1987

Related U.S. Application Data

[63] Continuation of Ser. No. 707,102, Feb. 28, 1985, abandoned.

[51] Int. Cl.$^4$ .................... A61K 39/12; A61K 39/245
[52] U.S. Cl. .................... 435/238; 424/89; 435/236
[58] Field of Search .................... 424/89, 90; 435/235–239

[56] References Cited

U.S. PATENT DOCUMENTS

| | | | |
|---|---|---|---|
| 4,522,810 | 6/1985 | Pedersen | 435/235 |
| 4,545,987 | 10/1985 | Giles et al. | 435/235 |
| 4,556,556 | 12/1985 | Wiesehahn et al. | 424/90 |
| 4,693,981 | 9/1987 | Wiesehahn et al. | 435/238 |
| 4,727,027 | 2/1988 | Wiesehahn et al. | 424/89 |
| 4,748,120 | 5/1988 | Wiesehahn et al. | 424/89 |

*Primary Examiner*—Shep K. Rose
*Attorney, Agent, or Firm*—Zarley, McKee, Thomte, Voorhees & Sease

[57] ABSTRACT

Novel vaccines for feline viral rhinotracheitis are prepared by psoralen inactivation of live Feline Herpesvirus I by exposure to ultraviolet radiation in the presence of an inactivating furocoumarin. The resulting inactivated viruses are suitable as the immunogenic substances in vaccines, which vaccines are useful for inoculation of hosts susceptible to feline virus rhinotracheitis.

10 Claims, No Drawings

FVR VACCINE

This is a continuation of copending application Ser. No. 707,102 filed on Feb. 28, 1985 now abandoned.

BACKGROUND OF THE INVENTION

1. Field of the Invention

Vaccination against both bacterial and viral diseases has been one of the major accomplishments of modern medicine. While effective vaccines have been developed for a large number of animal and human diseases, development of safe and effective vaccines for a number of other diseases remains problematic. In preparing suitable vaccines, the primary objectives are eliciting an immunogenic response which provides immunity against the disease of interest while assuring that the vaccine itself is non-pathogenic.

In preparing vaccines, a number of general approaches have been developed. The use of killed microbial agents as a vaccine, although generally safe, will not always be effective if the immunogenic characteristics of the agent are altered. In contrast, the preparation of live attenuated microbial agents as a vaccine will often provide improved immunologic reactivity, but will increase the risk that the vaccine itself will become pathogenic, e.g., as a result of reversion. Thus, although much experience has been gained over the years relating to the preparation of vaccines, the successful preparation of an effective vaccine against a particular infectious agent can never be assured, even when employing techniques which were previously successful for other microorganisms.

Feline viral rhinotracheitis (FVR) is species specific and enzootic in cat populations worldwide. The causative agent is a Herpesvirus (Feline Herpes I), and transmission is by direct contact or by infectious aerosols. Infection affects the nasal and ocular mucous membranes initially. Clinical signs, which commence within 2 to 10 days post infection, may include sneezing, coughing, lacrimation (excessive tearing), serous to mucopurulent nasal discharge, conjunctivitis, rhinitis, anorexia, dehydration, dyspnea, and severe depression. Cutaneous, ocular, nasal or oral ulcers and abortions may also be encountered. Pyrexia, up to 105° F. (40.5° C.), and a mild to moderate neutraphilic leukocytosis or mild anemia may be present. However, pyrexia and neutraphilia are mainly associated with secondary bacterial infection.

The course is often 1 to 3 weeks, but more prolonged systemic disease such as pneumonia or hepatitis may occur, especially in kittens. In fatal cases the course may extend to 4 or 5 weeks. Individual cats may die from the more severe manifestations or from secondary complications. At necropsy, respiratory tract lesions are most consistently encountered. These include hyperemic nasal and respiratory passages often covered with fibrinous or mucopurulent exudate. Secondary bacterial pneumonia may result in widely disseminated bacterial emboli. Microscopically, intranuclear inclusions, if present, occur most often in respiratory epithelium. Prior to the introduction of vaccines, 15% to 20% of isolated cat populations were reported to be asymptomatic carriers of FVR, providing a continuous reservoir for infection. Urban cat populations have carrier rates of 50% to 80%.

2. Description of the Prior Art

Feline viral rhinotracheitis was first recognized as a disease entity by Crandell and Mauer (1958) Proc. Soc. Expt. Bio. Med. 97:487–490. Experimental FVR infection results in low serum neutralizing antibody titers (e.g., 1:4 to 1:10). See, Crandall et al. (1961) J.A.V.-M.A., 138:191–196; and Hoover et al. (1970) Am. J. Path. 58:269–282. Individual cats may be resistant to reinfection with FVR, although they have little or no detectable serum antibody against FVR (Bartholomew et al. (1968) Cornell Vet. 58:248–265). Infection immunity is short-lived, and cats may be reinfected six months following a primary infection. Reinfection elicits mild clinical signs and reduced viral shedding (Walton and Gillespie (1970) Cornell Vet. 60:232–239).

Previous attempts at vaccine development for FVR have included formalin inactivation (Fisher, et al. (1966) VM/SAC 61:1182–1189; Tan et al. (1971) N.Z. Vet. J. 19:12–15; and Povey et al. (1978) Feline Pract. 8:36–42); temperature sensitive mutants (Slater et al. (1976) Develop. Biol. Stand. 33:410–416); and tissue culture attenuated live virus isolates (Bittle et al. (1974) VM/SAC 69:1503–1505; Bittle et al. (1975) Am. J. Vet. Res. 36:89–91; F. Scott (1975) Feline Practice Jan.-Feb.:17–22; and Edwards et al. (1977) VM/SAC Feb:205–209). Chemically inactivated FVR vaccines failed to induce immunity(Fisher et al. (1966) VM/SAC 61:1182–1189), although later trials with formalin inactivated FVR vaccines were somewhat successful (Tan et al. (1971) N.Z. Vet. J. 19:12–15 and Povey et al. (1978) Feline Pract. 8:36–42). Formalin inactivated FVR vaccines are critically dependent on the incorporation of a suitable immunologic adjuvant such as mineral oil.

One FVR vaccine production method utilized DNA inhibitors to select biochemically uncharacterized FVR mutants that were subsequently inactivated by UV irradiation (Davis et al. (1976) VM/SAC Oct:1405–1410). Inactivation was less than 100%, and the remaining live virus was cloned at 30° C. (±2° C.) and subjected to repeated cycles of the same process, resulting in an attenuated virus strain. See, U.S. Pat. No. 4,031,204. U.S. Pat. No. 4,287,178 discloses that temperature sensitive FVR mutants can be utilized as an attenuated live virus vaccine for FVR. Attenuated live FVR vaccines are efficacious, but may induce clinical disease or abortions. Combination vaccines have been described in which FVR and other feline pathogens are incorporated (Bittle et al. (1975) Feline Practice Nov.-Dec:13–15 and Edwards et al. (1977) Feline Practice July:4-5–50). These vaccines are also produced by standard procedures known to the art.

The preparation of psoralens and their use in inactivating viruses are described in U.S. Pat. Nos. 4,196,281 and 4,124,598.

SUMMARY OF THE INVENTION

Vaccines for inoculation against feline viral rhinotracheitis are prepared by irradiating live Feline Herpes I virus, the etiologic agent which causes FVR, with light in the presence of an inactivating furocoumarin compound for a time sufficient to render the virus completely non-infectious. It has been found that inactivated Feline Herpes I virus retains immunogenicity, and that inoculation of a susceptible host with such inactivated viruses elicits the production of serum neutralizing antibody and protects the host against subsequent challenge with live, infectious Feline Herpes I virus. The inactivated Feline Herpesvirus I may be combined with a physiologically-acceptable carrier or adjuvant, usually at from about $10^6$ to $10^9$ pfu/ml, to form the vaccine.

DESCRIPTION OF THE SPECIFIC EMBODIMENTS

Vaccines useful for the inoculation of feline hosts against feline viral rhinotracheitis are provided. The vaccines are prepared by inactivation of live Feline Herpes I virus in an appropriate medium with a sufficient amount of an inactivating furocoumarin to provide for inactivation of the virus upon subsequent irradiation with long wavelength ultraviolet (UV) radiation. The resulting inactivated virus may be stored until used for inoculation. Prior to inoculation, the inactivated virus will usually be combined with a physiologically-acceptable carrier or immunologic adjuvant.

Any of the isolates of Feline Herpes I virus, or combinations thereof, may be inactivated and utilized to prepare a vaccine according to the present invention. Such live, virulent viruses can be obtained from cats suffering from feline viral rhinotracheitis according to conventional techniques. See, e.g., Crandall and Mauer, supra.; Bittle et al. (1960) Amer. J. Vet. Res. 21:547; and Ditchfield and Grinyer (1965) Virology 26:504. Generally, virus obtained from the nasal and conjunctival membranes of infected cats are used to infect suitable feline cells grown in tissue culture. The viruses are replicated and isolated by serial passage following well known techniques. Alternatively, the virus may be derived from generally available sources, such as Feline Herpes I virus available from the American Type Culture Collection under designation VR636. A specific method for growing virus from seed virus is set forth in the Experimental section hereinafter.

In preparing the subject vaccines, the desired virus is grown in mammalian cell culture. Suitable cell lines include the AKD cell line (ATCC CCL 150) and Fc3Tg (ATCC CCL 176), and other cell lines permissive for Feline Herpes I virus and which can be grown in vitro as monolayer cultures or as suspension cultures. The cell cultures are grown to approximately 80% saturation density and infected with the feline herpesvirus at a multiplicity of infection (MOI), usually between about 0.03 and 0.3, preferably about 0.1. After adsorbing the viral inoculum to the cells by incubation for a limited period of time at a temperature in the range from about 35° C. to 40° C., an appropriate growth or maintenance medium is added. The cells are incubated at temperatures in the range from about 35° C. to 40° C., in the presence of about 5% carbon dioxide in air until at least about 50% of the cell culture exhibits cytopathic effect (CPE). CPE is characterized by cell rounding (in monolayers), cell detachment (from monolayers), and cell degeneration.

The culture vessel is shaken to detach loosely adhering cells and cellular debris, and the contents of each vessel are aseptically decanted into centrifuge bottles. The crude virus preparation is centrifuged at $10,000\times g$ for 30 minutes and the supernatant is discarded. The pellet is resuspended in one-twentieth the original volume of maintenance medium containing 7 to 10% (v/v) dimethyl sulfoxide (Sigma Chemical Co., St. Louis, MO 63178, cat. no. D 5879). For cell-associated virus preparations, the foregoing suspension is stored frozen at or below $-80°$ C. Cell-free virus preparations are produced from the foregoing suspension by freezing and thawing the suspension three times, centrifuging the resulting lysate at $10,000\times g$ for 30 minutes, and collecting and storing the virus-containing supernatant at or below $-80°$ C. Cell-free virus may also be prepared from a suspension which lacks dimethyl sulfoxide.

The particular growth and maintenance medium may be a conventional mammalian cell culture medium, such as Eagle's Minimum Essential Medium or Medium 199, usually supplemented with additives such as fetal bovine serum, fetal calf serum, broth prepared from dehydrated standard microbial culture media, or the like.

The furocoumarins useful for inactivation are primarily illustrated by the class of compounds referred to as psoralens, which includes psoralens and substituted psoralens where the substituents will be: alkyl, particularly having from 1 to 3 carbon atoms, e.g., methyl; alkoxy, particularly having from 1 to 3 carbon atoms, e.g., methoxy; and substituted alkyl having from 1 to 6, more usually from 1 to 3, carbon atoms and from 1 to 2 heteroatoms, which will be oxy, particularly hydroxy or alkoxy having from 1 to 3 carbon atoms, e.g., hydroxy methyl and methoxy methyl, or amino, including mono- and dialkyl amino or aminoalkyl, having a total of from 0 to 6 carbon atoms, e.g., aminomethyl. There will be from 1 to 5, usually from 2 to 4 substituents, which will normally be at the 4, 5, 8, 4' and 5' positions, particularly at the 4' position. Illustrative compounds include 5-methoxypsoralen; 8-methoxypsoralen (8-MOP); 4,5',8-trimethylpsoralen (TMP); 4'-hydroxymethyl-4,5',8-trimethylpsoralen (HMT); 4'-aminomethyl-4,5',8-trimethylpsoralen (AMT); 4-methylpsoralen; 4,4'-dimethylpsoralen; 4,5'-dimethylpsoralen; 4',8-dimethylpsoralen; and 4'-methyoxymethyl-4,5',8-trimethylpsoralen. Of particular interest are HMT, AMT and 8-MOP.

The furocoumarins may be used individually or in combination. Each of the furocoumarins may be present in amounts ranging from about 0.01 μg/ml to 1 mg/ml, preferably from about 5 μg/ml to 300 μg/ml, there not being less than about 1 g/ml nor more than about 1 mg/ml of furocoumarins.

In carrying out the invention the furocoumarin(s), in an appropriate solvent which is substantially inert and sufficiently polar to allow for dissolution of the furocoumarin(s), are combined with the viral suspension, conveniently a viral suspension in an aqueous buffered medium, such as used for storage. The amount of virus will generally be about $1\times 10^6$ to $10^{11}$, more usually about $1\times 10^7$ to $10^9$ and preferably about $1\times 10^8$ to $5\times 10^8$ pfu/ml. The furocoumarin will be at a concentration of about 0.001 mg/ml to 0.5 mg/ml, more usually about 0.02 mg/ml to 0.3 mg/ml. The amount of solvent which is used to dissolve the furocoumarin will be sufficiently small so as to readily dissolve in the aqueous viral suspension and have little, if any, effect on the results.

The furocoumarin may be added to the viral suspension in a single addition or in multiple additions, where the virus is irradiated between additions. Usually, the number of additions will be from about 1 to 50, more usually from about 10 to 40, and preferably from about 20 to 40. The total amount of furocoumarin which will be added will be sufficient to provide a concentration of at least about 0.01 mg/ml to about 1 mg/ml, usually not more than about 0.75 mg/ml. Since a substantial proportion of the furocoumarin will have reacted with the nucleic acid between additions, the total concentration of furocoumarin in solution will generally not exceed about 0.3 mg/ml.

The total time for the irradiation will vary depending upon the light intensity, the concentration of the furocoumarin, the concentration of the virus, and the manner of irradiation of the virus, where the intensity of the irradiation may vary in the medium. The total time will usually be at least about 2 hrs. and not more than about 80 hrs., generally ranging from about 10 hrs. to 50 hrs. The times between additions of furocoumarin, where the furocoumarin is added incrementally, will generally vary from about 30 min. to 24 hrs., more usually from about 1 hr. to 3 hrs.

The temperature for the irradiation is preferably under 25° C., more preferably under 20° C. and will generally range from about −10° C. to 15° C., more usually from about 0° to 10° C.

The irradiation is normally carried out in an inert atmosphere, where all or substantially all of the oxygen has been removed. Inert atmospheres include nitrogen, helium, argon, etc.

The light which is employed will generally have a wavelength in the range from about 300 nm to 400 nm. The intensity will generally range from about 0.1 mW/cm$^2$ to about 5W/cm$^2$.

Optionally, a small amount of a singlet oxygen scavenger may be included during the virus inactivation. Singlet oxygen scavengers include ascorbic acid, dithioerythritol, sodium thionite, glutathione, etc. The amount of scavenger will generally be at a concentration of about 0.001M to 0.5M, more usually at about 0.01M to 0.1M, where the addition may be made in a single or multiple additions.

During irradiation, the medium may be maintained still, stirred or circulated and may be either continuously irradiated or be subject to alternating periods of irradiation and non-irradiation. The circulation may be in a closed loop system or in a single pass system ensuring that all of the sample has been exposed to irradiation.

It may be desirable to remove the unexpended furocoumarin and/or its photobreakdown products from the irradiation mixture. This can be readily accomplished by one of several standard laboratory procedures such as dialysis across an appropriately sized membrane or through an appropriately sized hollow fiber system after completion of the irradiation. Alternatively, one could use affinity columns for one or more of the low molecular weight materials to be removed.

The inactivated virus may then be formulated in a variety of ways for use for inoculation. The concentration of the virus will generally be from about $10^6$ to $10^9$ pfu/ml, as determined prior to inactivation, with a total dosage of at least $10^5$ pfu/dose, usually at least $10^6$ pfu/dose, preferably at least $10^7$ pfu/dose. The total dosage will usually be at or near about $10^8$ pfu/dose, more usually being about $10^6$ to $10^7$ pfu/dose. The vaccine may include cells or may be cell-free. It may be an inert physiologically acceptable medium, such as ionized water, phosphate-buffered saline, saline, or the like, or may be adminstered in combination with a physiologically acceptable immunologic adjuvant, including but not limited to mineral oils, vegetable oils, mineral salts and immunopotentiators, such as muramyl dipeptide. The vaccine may be administered subcutaneously, intramuscularly, or intraperitoneally. Usually, a specific dosage at a specific site will range from about 0.1 ml to 4 ml, where the total dosage will range from about 0.5 ml to 8 ml. The number of injections and their temporal spacing may be highly variable, but usually 1 to 3 injections at 1, 2 or 3 week intervals are effective.

The following examples are offered by way of illusration, not by way of limitation.

EXPERIMENTAL

Materials and Methods

A. Virus Growth

Cat cell lines AKD (ATCC CCL150) or Fc3Tg (ATCC CCL176) were grown as monolayers in plastic cell culture vessels in a standard defined culture media consisting of Minimum Essential Medium (MEM) and Earles salts with non-essential amino acids (MEN); F12K; MEM; or alpha MEM. Medium was supplemented with 2% to 15% inactivated fetal calf serum ($F^i$) or 2% to 20% YELP (YELP consists of: yeast extract 5 g; lactalbumin hydrolysate 25 g; Bacto-peptone 50 g; deionized $H_2O$ 1000 mls sterilized by autoclaving or filtration). Cell cultures were used to produce live Feline Herpes I virus from master seed virus derived from Feline Herpes I virus (ATCC VR636). Cells were grown in culture vessels to 80% to 100% confluency (approximately $1 \times 10^5$ to $2 \times 10^5$ cells per cm$^2$ of growth surface area) using standard mammalian cell culture techniques as follows.

Corning plastic roller bottles (Corning No. 25140–850) with a growth surface area of 850 cm$^2$ containing 50 to 100 ml of MEN supplemented with 10% $F^i$ and $1 \times 10^8$ to $2 \times 10^8$ AKD or Fc3Tg cells/bottle were used for virus production. The cell cultures were initiated by seeding approximately $1 \times 10^6$ to $5 \times 10^6$ cells into 50 to 100 mls of growth medium in a roller bottle containing about 5% $CO_2$ in air and incubating the roller bottle on a roller bottle rotator at 1 to 5 rpm at 35° C. to 38° C. The cultures were grown to 80% to 100% confluency over a 7 to 14 day period with a 100% medium change every 3 to 5 days.

When the monolayers were 80% to 100% confluent, the culture medium was removed and the monolayer was washed with 20 to 50 mls of phosphate buffered saline (PBS) pH 7.2 to 7.4 (NaCl 8 g+KCl 0.2 g+Na$_2$HPO$_4$ 1.14 g+KH$_2$PO$_4$ 0.2 g). The PBS wash was discarded, and the roller bottle was infected by the addition of approximately $1 \times 10^7$ to $2 \times 10^7$ plaque forming units (pfu) of Feline Herpes I virus in 10 mls of PBS containing 2% $F^i$. The multiplicity of infection (MOI) was approximately 0.1. The virus inoculum was adsorbed to the cells by incubation at 35° C. to 38° C. for one hour at 1 to 5 rpm. The inoculation fluid was removed and 50 mls of MEN containing 10% $F^i$ was added per roller bottle. The post-infection incubation was at 35° C. to 38° C. in 5% $CO_2$ in air with rotation. Herpesvirus cytopathic effect (CPE) was evident forty to forty-eight hours post-infection. The CPE was characterized by cell rounding, cell detachment, and cell degeneration.

The contents of the roller bottle were swirled 48 hours post-infection to remove loosely attached materials from the roller bottle walls, and the contents of the roller bottles were decanted into centrifuge bottles. The virus, cells, and cell debris were pelleted by centrifugation at 10,000×g for 30 minutes.

Cell associated (CA) virus was prepared by:
1. resuspending the 10,000×g pellet in approximately 5 ml of a resuspension medium containing 80 parts F12K, 10 parts Fi, and 10 parts dimethylsulfoxide (DMSO) for each original roller bottle;

2. freezing the resuspended CA virus at −20° C. for 1.5 to 2 hours; and 3. transferring the CA virus frozen at −20° C. to temperatures ranging from −80° C. to −100° C.

Cell free (CF) virus is prepared by:
1. resuspending the 10,000×g pellet in F12K;
2. freezing and thawing the resuspended material 3 times;
3. clarifying the freeze-thawed material by centrifugation at 10,000×g for 30 minutes; and
4. freezing the clarified supernatant (CF virus) at temperatures ranging from −80° C. to −100° C.

CF or CA virus was thawed by gentle agitation at 37° C. in a water bath.

B. Virus Assay

Confluent monolayers of Fc3Tg or AKD cells were prepared in 6 cm diameter mammalian cell culture plastic petri dishes (Corning No. 25010). The growth medium used for Fc3Tg cells was MEN+10% $F^i$ and the growth medium used for AKD cells was F12K +15% $F^i$. Ten fold serial dilutions of virus samples were made by adding 0.5 ml of the virus sample to 4.5 mls of PBS +2% $F^i$ in a screw cap tube. The growth medium was removed from a 6 cm culture dish cell monolayer, 1.0 ml of virus sample (undiluted or diluted) was added, and the virus was adsorbed to the monolayer for 2 hours at 35° C. to 38° C. Two or more dishes were used for each sample. The unadsorbed inoculum was removed, and 4 mls of overlay medium was added per 6 cm culture dish. The overlay medium was prepared by mixing equal parts solution A (100 ml 2×MEM with L-glutamine, GIBCO #320-1935, +4 ml $F^i$) and 1% methyl cellulose (4,000 centipoises) in deionized $H_2O$ (Fisher M-281 sterilized by autoclaving). After the overlay was added the cultures were incubated at 35° C. to 38° C. in 5% $CO_2$ in air for at least 48 hours and examined for virus plaques which appeared as either open circular areas in the monolayer with rounded cells at the edge of the open area or as foci of multinucleated syncytial cells. The virus titer in pfu/ml was calculated by multiplying the average number of plaques per dish by the reciprocal of the dilution. The pfu/ml was the value used to determine the amount of virus needed to infect cells at a MOI of approximately 0.1. The pfu/ml in a virus preparation prior to inactivation was used to determine the immunizing dose.

C. Inactivation of Cell Free Virus (CF-FVR)

Nineteen mls of CF-FVR ($1.9 \times 10^7$ pfu/ml) were mixed with 0.4 ml of hydroxymethyltrioxsalen (HMT; 1 mg/ml in DMSO) and 1.9 ml of sodium ascorbate (0.1 M in $H_2O$). The mixture was prepared in 150 $cm^2$ tissue culture flasks (T-150, Corning No. 25120) that were subsequently deaerated for 2 minutes with pure argon gas. The virus-containing flasks were irradiated for 55 minutes at 4° C. using G.E. BLB fluorescent bulbs at an intensity of 1.5 $mW/cm^2$. The FVR/HMT/ascorbate mixture was then transferred by pipet into a second T-150 flask, which was deaerated for 2 minutes using pure argon gas. The second T-150 flask was irradiated for an additional 28 minutes at 4° C. under the same long wavelength UV light source.

The CF-FVR preparation was stored at -100° C. in a REVCO freezer. Subsequently the CF-FVR preparation was thawed and placed into a T-150 flask. The flask was deaerated with pure argon gas for 2 minutes and irradiation was continued as described above for an additional 15 hours and 40 minutes.

D. Inactivation of Cell Associated Virus (CA-FVR)

Cells from 10 roller bottles (about $1 \times 10^8$ to $2 \times 10^8$ cells/roller bottle) were resuspended in 28 mls of cell culture media. Twenty mls of the suspension were placed into a T-150 flask. To this flask was added 2 ml of freshly prepared sterile 0.1 M sodium ascorbate and 0.4 ml HMT (1 mg/ml in DMSO). The flask was deaerated with pure argon gas for 2 minutes, and the flask was irradiated at 4° C. using G.E. BLB fluorescent bulbs at an intensity of 1.5 $mW/cm^2$ for 75 minutes. The viral suspension was then transferred by pipet from the T-150 flask into a second T-150 flask and again deaerated with pure argon gas for 2 minutes. Irradiation was continued for an additional 95 minutes. The CA-FVR preparation was adjusted to 10% DMSO and the suspension was frozen at −20° C. for 1 hour and then stored at −100° C. in a REVCO freezer.

The stored frozen CA-FVR preparation was subsequently thawed, and the cells were pelleted in a clinical centrifuge. The cells were resuspended in 21 mls of serum-free medium to which 2.1 mls of freshly prepared 0.1 M sodium ascorbate and 0.4 ml of HMT (1 mg/ml in DMSO) were added. The sample was transferred by pipet to a T-150 flask, and irradiation was continued for an additional 15 hours and 40 minutes.

E. Assessment of Inactivation by Blind Passage

Fc3Tg or AKD cells were grown to confluency in 850 $cm^2$ roller bottles using standard cell culture procedures as described above. The culture medium was removed from the roller bottle, and 2.0 mls of the inactivated virus preparation, mixed with 18 mls of medium containing 2% $F^i$, were adsorbed to the roller bottle cell monolayer for 60 minutes at 35° C. to 38° C. with rotation at 1 to 5 rpm. After adsorption, the inoculum was removed and 150 ml of maintenance medium (MEN or F12K with 2% $F^i$) added. The roller bottle culture was then incubated at 35° C. to 38° C. for 7 days with daily observation for viral CPE (see plaque assay above for description of CPE). The roller bottle culture received a 100% medium change after 3 to 5 days. If no CPE was observed during the first roller bottle passage, the cell monolayer was scraped into the maintenance medium which was then decanted into a centrifuge bottle. The cells were pelleted by centrifugation at room temperature at 1,000×g for 15 minutes, resuspended in 20 ml of fresh maintenance medium, and passed to a new confluent roller bottle culture of Fc3Tg or AKD cells as described above. The second roller bottle blind passage was observed for 7 days and fed once on day 3 to 5. If no CPE was observed during the second roller bottle blind passage, a third roller bottle blind passage was performed. If no CPE was observed by the end of the third roller bottle passage, the virus preparation was considered inactive.

F. Administration Procedure

Photochemically inactivated FVR is inoculated via syringe into cats by either single or multiple routes, including but not limited to intravenously (IV), subcutaneously (SQ), intramuscularly (IM), or intraperitoneally (IP). The vaccine is administered in various volumes (0.5 to 3.0 ml) and in various concentrations ($10^6$ to $10^8$ pfu; either CF, CA or in combination). In the following examples the vaccine was administered in combination with aluminum hydroxide as an immunologic adjuvant. The number of injections and their temporal spacing was as set forth in each example.

RESULTS

A. Inoculation with CF-FVR

The experimental group consisted of four specific pathogen free kittens (2 males, 2 females) four months old (Liberty Laboratories, Liberty Corner, N.J.). The control group consisted of two similar female kittens. The experimental group was inoculated IM with $3 \times 10^7$ pfu (3 mls) of HMT inactivated CF-FVR on days 0 and 21, and again inoculated with $3 \times 10^7$ pfu HMT inactivated with an equal amount of 2% aluminum hydroxide [Al(OH)$_3$] adjuvant on day 61. Controls were vaccinated at eight weeks and at thirteen weeks of age with a commercial FVR vaccine using the manufacturer's recommended procedure. Serum samples were collected weekly and tested for anti-FVR neutralizing antibodies.

Following live virus challenge (10$^6$ pfu intranasally and intraconjunctivally), a numerical scoring system (Table 1) was used to assess the clinical response to both experimental and control cats.

TABLE 1

Scoring System for Clinical Effects of Herpesvirus Challenge in Cats

| Factor | Degree | Score |
|---|---|---|
| Fever | 101 to 102° F. | 0 |
|  | 102 to 103 | 1 |
|  | 103 to 104 | 3 |
|  | greater than 104 | 5 |
| Depression | slight | 1 |
|  | moderate | 3 |
|  | severe | 5 |
| Sneezing | occasional | 1 |
|  | moderate | 3 |
|  | paroxysmal | 5 |
| Lacrimation | serous | 1 |
|  | mucoid | 3 |
|  | purulent | 5 |
| Nasal Discharge | serous | 1 |
|  | mucoid | 3 |
|  | purulent | 5 |
| Appetite | normal; eats all food | 0 |
|  | fair; eats more than ½ of food | 1 |
|  | poor, eats less than ½ of food | 3 |
|  | none; eats nothing | 5 |

Three of four experimental cats developed serum neutralizing anti-FVR antibody (SN) titers of 1:2 that were detected between day 42 and day 58. Following the third immunization (day 61), four of four experimental cats had SN titers of 1:4 (day 80). Baseline SN antibody titers on the experimental cats were negative. The control cats did not develop detectable SN antibody titers during the pre-challenge period.

All cats were exposed to 10$^6$ pfu of live FVR by intraconjunctival and intranasal injection on day 91. Each cat was monitored twice daily for the absence, presence and degree of severity of factors given in Table 1. A composite clinical score was derived for each cat after a 15 day observation period.

Three of four experimental cats demonstrated mild temperature elevation and serous ocular or nasal discharge along with mild intermittent depression and appetite suppression. Their composite scores were 39, 42, and 35 respectively for the 15 day observation period. The fourth experimental cat was more severly affected (composite score =84) by moderate, but transient, sneezing and mucoid nasal discharge. Both control cats were severely affected by live virus challenge. Severe purulent nasal and ocular discharge and lack of appetite were apparent. The control cats had composite scores of 133 and 253.

Three weeks following live FVR challenge, all cats were tested for SN antibody titers against FVR. Three of four experimental cats had SN antibody titers of 1:16 while the fourth cat had a 1:8 titer. One of the control cats had an SN antibody titer of 1:4 while the second control lacked an SN antibody titer against FVR.

B. Inoculation with CA-FVR

Nine age-matched specific pathogen free kittens, 4 months old (Liberty Laboratories, Liberty Corner, N.J.), were randomly assigned to three experimental groups designated A, B, and C.

Group A (controls) was inoculated twice with 1 ml tissue culture fluid and 1 ml aluminum hydroxide adjuvant. Group B was inoculated twice with a commercial FVR vaccine according to the manufacturer's recommendation. Group C was inoculated three times with 10$^7$ HMT-inactivated CA-FVR in aluminum hydroxide (total volume =2 ml; 1:1 vaccine to adjuvant). All injections were given IM at three week intervals.

Live FVR virus (10$^6$ pfu intranasally and intraconjunctivally) was given on day 63 and a numerical scoring system (Table 1) was used to assess the kittens' clinical response for a 15 day post-challenge period. Serum samples were collected from all kittens prior to vaccination, prior to the second and third immunizations, prior to live FVR challenge, and at 15 days post-challenge. The sera were utilized to assess neutralizing antibody titers by standard procedures.

The control kittens (Group A) maintained SN antibody titers less than 1:2 (negative) throughout the pre-challenge period. Fifteen days following live FVR challenge Group A kittens uniformly had SN antibody titers of 1:2. Kittens in Groups B and C lacked detectable anti-FVR antibody titers pre-immunization, but all kittens in Groups B and C had SN antibody titers of 1:2 or 1:4 after two immunizations. The third immunization in Group C kittens did not significantly alter their SN antibody titers. Following a 15 day post-challenge period, kittens in Groups B and C demonstrated an anamnestic immunologic response, with SN antibody titers ranging from 1:16 to 1:64.

Clinically, Group A kittens were severely affected by live FVR challenge, whereas kittens in Groups B and C were significantly protected by their respective vaccines.

The composite clinical scores for Group A were 125, 141, and 128 for the 15 day post-challenge period. The composite clinical scores for Group B were 25, 20, and 64, while Group C had composite clinical scores of 21, 15, and 34. The clinical signs evident were characteristic of FVR.

From the SN data and clinical scoring, it is evident that kittens immunized with the experimental HMT-inactivated FVR vaccines (cell-free or cell associated) in the above examples were significantly immune to the clinical effects of severe FVR challenge.

According to the present invention, furocoumarin-inactivated feline herpesvirus I retains its immunogenicity and is suitable as the immunogenic substance in a vaccine against feline viral rhinotracheitis. The inactivated virus of the present invention is non-infectious and is safe when administered to a host for vaccination.

Although the foregoing invention has been described in some detail by way of illustration and example for purposes of clarity of understanding, it will be obvious that certain changes and modifications may be practiced within the scope of the appended claims.

What is claimed is:

1. A method of making a vaccine useful for inoculation of a feline host susceptible to feline virus rhinotracheitis, said method comprising:
   (1) inactivating at least one feline Herpesvirus I isolate by
      (a) adding to said feline Herpesvirus I isolate a small but inactivating effective amount of a furocoumarin; and thereafter
      (b) exposing said feline Herpesvirus I to ultraviolet light having a wavelength within the range of from about 300 nm to 400 nm and an intensity of from about 0.1 mW/cm$^2$ to 5 W/cm$_2$ at a temperature below about 40° C. for a time sufficient to render said virus noninfectious without destroying the characteristic immunologenic response of said feline Herpesvirus I isolate.

2. The method according to claim 1 wherein said furocoumarin is 4'-hydroxymethyl-4,5',8-trimethylpsoralen.

3. The method of claim 1 wherein said inactivating occurs in the substantial absence of oxygen.

4. The method according to claim 1 wherein said virus is inactivated in the presence of a singlet oxygen scavenger.

5. The method according to claim 1 wherein said virus is grown in substantially confluent monolayers of host cells immediately prior to said inactivating procedure.

6. A method of preparing a vaccine useful for inoculation of a feline host susceptible to feline virus rhinotracheitis, said method comprising:
   subjecting at least one inactivated feline Herpesvirus I isolate to ultraviolet light having a wavelength within the range of from about 300 nm to 400 nm and an intensity of from about 0.1 mW/cm$^2$ to 5W/cm$^2$ at a temperature below about 40° C. in the presence of an inactivating furocoumarin for a time sufficient to render said virus noninfectious without destroying its chacteristic immunogenic response.

7. The method according to claim 6 wherein said furocoumarin is 4'-hydroxymethyl-4,5',8-trimethylpsoralen.

8. The method of claim 6 wherein said inactivating occurs in the substantial absence of oxygen.

9. The method according to claim 6 wherein said virus is inactivated in the presence of a singlet oxygen scavenger.

10. The method according to claim 6 wherein said virus is grown in substantially confluent monolayers of host cells immediately prior to said inactivating procedure.

* * * * *